(12) United States Patent
Kolter et al.

(10) Patent No.: US 9,795,576 B2
(45) Date of Patent: Oct. 24, 2017

(54) PROTECTIVE COATINGS FOR ACIDIC ACTIVE INGREDIENTS

(75) Inventors: Karl Kolter, Limburgerhof (DE); Maximilian Angel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 723 days.

(21) Appl. No.: 13/246,324

(22) Filed: Sep. 27, 2011

(65) Prior Publication Data

US 2012/0076834 A1    Mar. 29, 2012

Related U.S. Application Data

(60) Provisional application No. 61/386,565, filed on Sep. 27, 2010.

(51) Int. Cl.
| | | |
|---|---|---|
| *A61K 31/616* | (2006.01) | |
| *A61K 9/00* | (2006.01) | |
| *A61K 31/192* | (2006.01) | |
| *A61K 9/50* | (2006.01) | |

(52) U.S. Cl.
CPC .......... *A61K 31/192* (2013.01); *A61K 9/5073* (2013.01); *A61K 31/616* (2013.01)

(58) Field of Classification Search
None
See application file for complete search history.

(56) References Cited

U.S. PATENT DOCUMENTS

| | | | |
|---|---|---|---|
| 3,070,509 | A | 12/1962 | Völker et al. |
| 3,853,594 | A | 12/1974 | Moroff et al. |
| 4,112,215 | A | 9/1978 | Boessler et al. |
| 4,181,708 | A | 1/1980 | Dannelly |
| 4,181,710 | A | 1/1980 | Dannelly et al. |
| 4,433,076 | A | 2/1984 | Bauer et al. |
| 4,452,862 | A | 6/1984 | Markert et al. |
| 4,705,695 | A | 11/1987 | Lehmann et al. |
| 5,578,316 | A | 11/1996 | Bhardwaj et al. |
| 5,837,277 | A | 11/1998 | Hayward |
| 6,624,210 | B1 | 9/2003 | Petereit et al. |
| 6,696,085 | B2 | 2/2004 | Rault et al. |
| 2001/0007680 | A1 | 7/2001 | Kolter et al. |
| 2003/0064036 | A1 | 4/2003 | Petereit et al. |
| 2003/0220413 | A1 | 11/2003 | Petereit et al. |
| 2004/0249035 | A1* | 12/2004 | Petereit ................ A61K 9/1635 524/394 |
| 2006/0093680 | A1* | 5/2006 | Humar ................ A61K 9/2009 424/490 |
| 2006/0204587 | A1 | 9/2006 | Kolter et al. |
| 2008/0299194 | A1 | 12/2008 | Kolter et al. |
| 2009/0197958 | A1* | 8/2009 | Sastry ................ A61K 9/1676 514/563 |
| 2010/0048760 | A1 | 2/2010 | Kolter et al. |
| 2011/0033532 | A1* | 2/2011 | Angel ................ A61K 9/2018 424/465 |
| 2012/0076858 | A1 | 3/2012 | Kolter et al. |

FOREIGN PATENT DOCUMENTS

| | | | |
|---|---|---|---|
| CA | 2570277 A1 * | 2/2006 | |
| DE | WO 2009016258 A1 * | 2/2009 | .......... A61K 9/2018 |
| EP | 1110544 | 6/2001 | |
| IN | WO 2005055986 A1 * | 6/2005 | .......... A61K 9/1635 |
| WO | WO-00/05307 | 2/2000 | |
| WO | WO-02/067906 | 9/2002 | |
| WO | WO-03/075896 | 9/2003 | |
| WO | WO-2004/019918 | 3/2004 | |
| WO | WO 2006010394 A2 * | 2/2006 | |
| WO | WO-2007/071581 | 6/2007 | |
| WO | WO-2008/080774 | 7/2008 | |
| WO | WO-2009/016258 | 2/2009 | |
| WO | WO-2010/139654 | 12/2010 | |

OTHER PUBLICATIONS pKa Table from the David Evans Research Group at Harvard University, downloaded Jul. 2, 2012, from the internet site: http://evans.harvard.edu/pdf/evans_pka_table.pdf.*
"International Search Report from PCT/EP2011/066627", mailed on Nov. 25, 2011 , 3 pages.
EUDRAGIT E 100 Product Sheet, 1 pg.
EUDRAGIT L 30 D-55 Product Sheet, 1 pg.
EUDRAGIT S 100 Product Sheet, 1 pg.

* cited by examiner

*Primary Examiner* — Frederick Krass
*Assistant Examiner* — Michael P Cohen
(74) *Attorney, Agent, or Firm* — Servilla Whitney LLC

(57) ABSTRACT

Dosage forms provided with protective coatings in which a core comprising at least one acidic active ingredient is provided with at least one inner and one outer coating layer, where the outer layer comprises, as component A, a cationic polymer which is an emulsion polymer of N,N-diethylaminoethyl methacrylate and further monomers.

17 Claims, No Drawings

PROTECTIVE COATINGS FOR ACIDIC ACTIVE INGREDIENTS

CROSS-REFERENCE TO RELATED APPLICATIONS

This application claims priority under 35 U.S.C. §119(e) to U.S. Provisional Application No. 61/386,565, filed Sep. 27, 2010, the disclosure of which is incorporated herein by reference in its entirety.

FIELD

The present invention generally relates to protective coatings for pharmaceutical dosage forms containing acidic active ingredients, particularly film coatings based on a cationic polymer which is obtained by means of free-radical emulsion polymerization of a monomer mixture comprising N,N-diethylaminoethylmethacrylate.

BACKGROUND

DE-B 1090381 describes a method of covering pharmaceuticals with coating masses soluble in the stomach. These comprise a copolymer of 20 to 80% of at least one amino ester of (meth)acrylic acid and 80 to 20% of a monomer which forms a water-insoluble polymer as homopolymer. Specific examples of suitable polymerizable amino esters that are given are the esters of acrylic acid and (meth)acrylic acid with N,N-dimethylaminoethanol, N,N-diethylaminoethanol, N,N-dimethylaminopropanol and N-(hydroxyethyl)morpholine. Suitable co-monomers that are mentioned are lower esters of acrylic acid and preferably of (meth)acrylic acid, such as ethyl acrylate, methyl, butyl and hexyl (meth)acrylate. The preparation takes place by solution polymerization in an organic solvent; a working example is not given.

DE-B 1219175 describes a method of producing veterinary medicine active ingredient preparations which are protected against the effect of rumen juices of ruminants. For this, these preparations are coated with copolymers which comprise, in copolymerized form, N,N-dialkylaminoalkyl (meth)acrylamides and a co-monomer which is selected from (meth)acrylates, acrylonitrile and vinyl aromatics. Co-polymers based on N,N-dialkylaminoalkyl(meth)acrylates are regarded as disadvantageous according to the teaching of this document since the ester group, compared to amide group, rather saponifies in the basic medium.

DE-A 2135073 describes coating compositions for pharmaceuticals which comprise an aqueous polymer dispersion, where the polymer is composed to 10 to 55% by weight of monomers with a carboxyl group and/or aminoalkyl- or dialkylaminoalkylester group. A suitable monomer that is specified is, beside a large number of others, also diethylaminoethylmethacrylate (DEAEMA). Suitable co-monomers that are mentioned are the lower esters of (meth)acrylic acid, preferably methyl methacrylate, (meth)acrylonitrile, vinyl aromatics, vinylchloride and vinylacetate. The preparation takes place by aqueous emulsion polymerization, preferably by the emulsion feed method. Specific emulsion polymers based on DEAEMA are not disclosed.

For providing binders for pharmaceutical coatings with a low residual monomer content, DE-B 2512238 teaches the use of a powder obtained by spray-drying a polymer dispersion for producing coating solutions for these pharmaceuticals. As regards the dispersions used for the spray-drying, reference is made to DE 1090381, DE 1219175 and DE 2135073.

DE-A 2838278 describes coatings for oral administration forms for ruminants comprising a) at least one film-forming polymer with at least one basic amino group and with a nitrogen content of from 3 to 14% which is soluble in aqueous rumen medium at a pH above 5.5 within 24 hours, and b) at least one hydrophobic substance dispersed in the polymer which is selected from $C_{12}$-$C_{32}$-fatty acids, Al salts of these fatty acids and/or polycarboxylic acids.

To produce the coating, a solution in an organic solvent is used. A large number of nitrogen-containing homopolymers and copolymers is listed as suitable polymers, without discussing suitable processes for their preparation. Working example 29 here gives a copolymer of 40% N,N-diethylaminoethylmethacrylate, but without stating a process for its preparation.

GB 1324087 describes coating polymers for oral administration forms for ruminants which comprise a) at least one N,N-dialkylaminoalkyl(meth)acrylate and b) at least one ethylenically unsaturated compound which is selected from vinyl aromatics and derivatives thereof, vinyl esters, esters of (meth)acrylic acid and acrylonitrile in copolymerized form. Suitable monomers a) that are disclosed are N,N-dimethylaminoethylmethacrylate (DMAEMA) and tert-butylaminoethylmethacrylate (TBAEMA). As co-monomer b), in particular methylmethacrylate is considered to be unsuitable since it has a tendency to form excessively brittle coatings. Bulk polymerization, suspension polymerization, solution polymerization and emulsion polymerization are stated as suitable polymerization processes. The copolymers in the working examples were produced by solution polymerization.

DE 3426587 A1 describes a process for coating pharmaceutical forms by applying a film of a liquid, film-forming coating composition which comprises a dissolved polymer with pendant tertiary ammonium salt groups. To produce these polymer solutions, it is possible to convert, inter alia, copolymers based on N,N-dialkylaminoalkyl(meth)acrylates with aqueous inorganic or organic acids into aqueous ammonium salt solutions.

DE 3049179 A1 is an application of addition to DE 2512238 and relates to the use of a powder obtained by spray-drying in accordance with the teaching of the last-mentioned document in the form of an aqueous suspension which additionally comprises a plasticizing agent for producing coatings by thermal gelation.

EP 0058765 A2 describes coating compositions for pharmaceutical forms that are soluble or swellable in gastric juice which comprise, as binder, an emulsion polymer based on N,N-dialkylaminoalkyl(meth)acrylates, there being located between the amino group and the (meth)acrylate group a branched alkylene or aralkylene group having at least three carbon atoms arranged in a straight chain.

WO 2005/055986 and WO 2005/056619 describe polymers with pH-dependent swelling/dissolving behavior and their use in pharmaceutical forms.

WO 00/05307 deals with the provision of coatings and binders for pharmaceutical forms which comprise (meth)acrylate copolymers which have monomer radicals with tertiary amino groups, the aim being that simple dry or aqueous further processing be possible. For this, this document teaches a process in which (a) a copolymer of $C_1$-$C_4$ esters of (meth)acrylic acid and (meth)acrylate monomers which have tertiary ammonium groups, (b) a plasticizer and (c) an emulsifier with an HLB value of at least 14 are blended together, and the coating composition or binder is prepared there from by melting, pouring, spreading or spraying, where the copolymer (a) is introduced in powder form with an average particle size of from 1 to 40 µm. The processability achieved in this case is attributed to the provision of the copolymer (a) in powder form with an extremely small particle size.

WO 02/067906 relates to coatings and binders with improved water vapor permeability compared with those described in WO 00/05307. Here, the coatings and binders are prepared with a mixture which comprises (a) a copolymer of $C_1$-$C_4$ esters of (meth)acrylic acid and further (meth)acrylate monomers with functional tertiary ammonium groups in powder form with an average particle size of from 1 to 40 µm, (b) an emulsifier with an HLB value of at least 14 and (c) a $C_{12}$-$C_{18}$-monocarboxylic acid or a $C_{12}$-$C_{18}$-hydroxyl compound.

WO 2004/019918 describes coatings and binders which correspond in terms of their composition to those described in WO 00/05307 and WO 02/067906.

According to U.S. Pat. No. 6,696,085 B2, a methacrylic acid copolymer type C should be used as disintegrant. The methacrylic acid copolymer type C is an enteric polymer which is not soluble in the acidic pH range, but is water-soluble in the pH range of 7, as is present in the oral cavity. Besides a low fracture strength (<20N), the tablets have high friability (>7%) and include a high proportion, in the region of 15% by weight, of a coarsely particulate disintegrant. Consequently, they have low mechanical strength and, on account of the high proportion of coarsely particulate disintegrant, have an unpleasant sandy feel in the mouth.

The matrix components based on sugar alcohols, disintegrants and insoluble polymers are generally known for pharmaceutical applications from WO 2007/071581.

WO 2009/016258 discloses the preparation of aqueous polymer dispersions of cationic polymers based on N,N-diethylaminoethylmethacrylate as are used according to the invention, and their use for coating pharmaceuticals. This specification also describes the application of said polymers to ibuprofen pellets. However, it has turned out that these preparations are not storage-stable, become sticky upon storage, the taste masking deteriorates and the release is altered massively.

SUMMARY

One aspect of the present invention relates to protective coatings for pharmaceutical dosage forms containing acidic active ingredients. These film coatings are based on a cationic polymer which is obtained by means of free-radical emulsion polymerization of a monomer mixture comprising N,N-diethylaminoethyl methacrylate and further monomers, and the coatings comprise at least one inner layer and one outer layer.

According to one or more embodiments of this aspect, at least one acidic active ingredient comprises an active ingredient with free carboxyl, sulfonic acid or phosphonic acid groups, acidic hydroxyl groups, acidic N—H groups or acidic C—H groups or mixtures of such active ingredients. In one or more embodiments, the acidic active ingredients have a pKa value between 6.5 and 0.5. In further embodiments, acidic active ingredients with a pKa value between 5.0 and 1.0.

In certain embodiments, the inner coating layer comprises a neutral water-soluble polymer. The neutral polymer of the inner coating layer comprises polyvinyl alcohols, polyalkylene glycol—polyvinyl alcohol graft copolymers, polyvinylpyrrolidones, vinylpyrrolidone—vinyl acetate copolymers, alkylated and hydroxyalkylated celluloses or starches or mixtures of such polymers. In particular embodiments, the neutral polymer of the inner coating layer comprises polyvinyl alcohols, polyalkylene glycol—polyvinyl alcohol graft copolymers or mixtures thereof.

According to one or more embodiments, component A of the outer coating layer comprises a polymer obtained by free-radical polymerization of:
  a) N,N-diethylaminoethyl methacrylate, and
  b) at least one free-radically polymerizable compound selected from esters of α,β-ethylenically unsaturated mono- and dicarboxylic acids with $C_1$-$C_8$-alkanols.

Certain embodiments provide methyl methacrylate as monomer b).

In one or more embodiments, component A of the outer coating layer comprises a polymer of 43 to 47% by weight, based on the total weight of the monomers used for the polymerization, of N,N-diethylaminoethyl methacrylate a), and 53 to 57% by weight, based on the total weight of the monomers used for the polymerization, of at least one compound b).

Certain embodiments provide that the outer coating layer further comprises, as component B, one or more antioxidants. In one or more embodiments, the antioxidants are selected from the group consisting of phenolic antioxidants, thiolic antioxidants, basic amino acids, alkali metal carbonates and alkali metal bicarbonates.

According to one or more embodiments, the outer coating layer further comprises, as component C, one or more plasticizers. In certain embodiments, one or more plasticizers are selected from the group consisting of tributyl citrate, acetyltributyl citrate, acetyltriethyl citrate, triacetin, triethyl citrate, diethyl sebacate and dibutyl sebacate.

One or more embodiments provide that the outer coating layer further comprises, as component D, one or more pharmaceutical excipients selected from the group consisting of aroma substances, taste-improving substances, sweeteners, glidants, wetting agents, release agents, antiadhesives, stabilizers, pore formers, neutralizing agents, polishes, dyes, pigments, disinfectants or preservatives, and thickeners.

In one or more embodiments, the inner coating layer has a layer thicknesses of from 1 to 50 µm. In further embodiments, the inner coating layer has a layer thicknesses of from 2 to 25 µm. In still further embodiments, the inner coating layer has a layer thicknesses of from 5 to 15 µm.

According to certain embodiments, the outer coating layer has a layer thicknesses of from 5 to 200 µm. Further embodiments provide an outer coating layer with a layer thicknesses of from 10 to 150 µm. A particular embodiment provides an outer coating layer with a layer thicknesses of from 20 to 100 µm.

DETAILED DESCRIPTION

According to one or more embodiments of the present invention, provided are improved film coatings for pharmaceutical administration forms comprising acidic active ingredients which, even upon prolonged or thermally stressful storage, do not have any change in taste masking, protection against moisture and in the release behavior, and which do not have the disadvantages of the prior art.

Accordingly, protective coatings and administration forms provided with such coatings have been found in which a core comprising at least one acidic active ingredient is provided with at least one inner and one outer coating layer, where the outer layer comprises a cationic polymer which is an emulsion polymer of N,N-diethylaminoethylmethacrylate and further monomers.

Within the context of one or more embodiments of the invention, acidic active ingredients are understood as meaning active ingredients with free carboxyl, sulfonic acid or phosphonic acid groups, acidic hydroxyl groups, acidic N—H groups or acidic C—H groups. The pKa value of these active ingredients is between 6.5 and 0.5, preferably between 5.0 and 1.0. The pKa value refers the negative $\log_{10}$ log of the acid constant. The acid constant is usually ascertained by titration with hydroxide solution.

The coating according to certain embodiments of the invention has an at least two-layer structure, with an inner layer consisting of a neutral water-soluble polymer and optionally pigments and further pharmaceutically customary excipients. A neutral water-soluble polymer is to be understood as meaning a polymer without acidic or basic group. Water-soluble means that at 25° C. at least 50 g are soluble in 1 L of water.

In one or more embodiments, the outer layer comprises:
i) as component A, a polymer obtained by free-radical polymerization, of
  a) N,N-diethylaminoethylmethacrylate, and
  b) at least one free-radically polymerizable compound selected from esters of α,β-ethylenically unsaturated mono- and dicarboxylic acids with $C_1$-$C_8$-alkanols,
ii) optionally as component B, one or more antioxidants,
iii) optionally as component C, one or more plasticizers,
iv) optionally as component D, further pharmaceutical excipients.

Water-soluble polymers of the inner layer which can be used are:
polyvinyl alcohols, polyalkylene glycol—polyvinylalcohol graft copolymers, polyvinylpyrrolidones, vinylpyrrolidone—vinylacetate copolymers, alkylated and hydroxyalkylated celluloses or starches, such as e.g. hydroxypropylcellulose, hydroxypropylmethylcellulose, hydroxyethylcellulose, methylcellulose, hydroxyethylstarch.

The layer thickness of the inner layer can be 1 to 50 μm, preferably 2 to 25 μm and particularly preferably 5 to 15 μm.

The layer thickness of the outer layer can be 5 to 200 μm, preferably 10 to 150 μm and particularly preferably 20 to 100 μm.

In certain embodiments, the coating compositions used for the outer layer are based on aqueous polymer dispersions which are obtained by free-radical emulsion polymerization of a monomer mixture M) comprising
a) N,N-diethylaminoethylmethacrylate, and
b) at least one free-radically polymerizable compound selected from esters of α,β-ethylenically unsaturated mono- and dicarboxylic acids with $C_1$-$C_8$-alkanols,
in an aqueous medium at a pH of at least 8.

The coating compositions in the form of aqueous polymer dispersions preferably comprise no additional organic solvents.

According to particular embodiments of the invention, the coating compositions serve for producing pharmaceutical dosage forms which should be rapid-releasing in the acidic environment of the stomach. I.e. the coatings are soluble in gastric juice. In this connection, rapidly-releasing means that after 60 min at least 80% of the active ingredient has been released. Coatings obtained according to embodiments of the invention should not dissolve in the oral cavity and throat in the neutral or virtually neutral environment of the saliva.

The coating compositions invention can be used for masking taste or for protecting against moisture. The water vapor permeability of the coatings is very low, as a result of which moisture-sensitive active ingredients are protected.

Component A
Monomer a)

According to certain embodiments of the invention, N,N-diethylaminoethylmethacrylate is used as monomer a).

To produce the aqueous polymer dispersions Pd) according to the invention, the component a) is used preferably in an amount of from 25 to 65% by weight, particularly preferably 30 to 60% by weight, in particular 38 to 48% by weight, specifically 43 to 47% by weight, based on the total weight of the monomers used for the polymerization.

Monomer b)

In one or more embodiments, the component b) is selected from esters of alpha, beta-ethylenically unsaturated mono- and dicarboxylicacids with $C_1$-$C_8$-alkanols.

Suitable compounds b) are methyl(meth)acrylate, methylethacrylate, ethyl(meth)acrylate, ethylethacrylate, n-propyl(meth)acrylate, isopropyl(meth)acrylate, n-butyl(meth)acrylate, sec-butyl(meth)acrylate, tert-butyl(meth)acrylate, tertbutylethacrylate, n-hexyl(meth)acrylate, n-heptyl(meth)acrylate, n-octyl(meth)acrylate, 1,1,3,3-tetramethylbutyl(meth)acrylate and ethylhexyl(meth)acrylate.

As component b), particular preference is given to using methylmethacrylate or a monomer mixture comprising methylmethacrylate.

To produce the aqueous polymer dispersions, the component b) is used preferably in an amount of from 35 to 75% by weight, particularly preferably 40 to 70% by weight, in particular 52 to 62% by weight, specifically 53 to 57% by weight, based on the total weight of the monomers used for the polymerization.

Monomer c)

The monomer mixtures M) used for producing the polymer dispersions can additionally comprise at least one further monomer c). The additional monomers c) are preferably selected from esters of alpha, beta-ethylenically unsaturated mono- and dicarboxylicacids with $C_9$-$C_{30}$-alkanols and $C_2$-$C_{30}$-alkanediols, amides of alpha, beta-ethylenically unsaturated mono- and dicarboxylic acids with $C_2$-$C_{30}$-amino alcohols which have a primary or secondary amino group, primary amides of alpha, beta-ethylenically unsaturated monocarboxylic acids and N-alkyl and N,N-dialkyl derivatives thereof, N-vinyllactams, open-chain N-vinyl amide compounds, esters of vinyl alcohol and allylalcohol with $C_1$-$C_{30}$-monocarboxylic acids, vinyl ethers, vinyl aromatics, vinyl halides, vinylidene halides, $C_2$-$C_8$-mono olefins, unsaturated nitriles, non-aromatic hydrocarbons with at least two conjugated double bonds and mixtures thereof.

Suitable additional monomers c) are esters of alpha, beta-ethylenically unsaturated mono- and dicarboxylic acids with $C_9$-$C_{30}$-alkanols, such as n-nonyl(meth)acrylate, n-decyl(meth)acrylate, n-undecyl(meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arachinyl(meth)acrylate, behenyl(meth)acrylate, lignoceryl(meth)acrylate, cerotinyl(meth)acrylate, melissinyl(meth)acrylate, palmitoleinyl(meth)acrylate, oleyl(meth)acrylate, linolyl(meth)acrylate, linolenyl(meth)acrylate, stearyl(meth)acrylate, lauryl(meth)acrylate and mixtures thereof.

Suitable additional monomers c) are also esters of alpha, beta-ethylenically unsaturatedmono- and dicarboxylic acids with $C_2$-$C_{30}$-alkanediols, such as 2-hydroxyethylacrylate, 2-hydroxyethylmethacrylate, 2-hydroxyethylethacrylate, 2-hydroxypropylacrylate, 2-hydroxypropylmethacrylate, 3-hydroxypropylacrylate, 3-hydroxypropylmethacrylate, 3-hydroxybutylacrylate, 3-hydroxybutylmethacrylate, 4-hydroxybutylacrylate, 4-hydroxybutylmethacrylate, 6-hydroxyhexylacrylate, 6-hydroxyhexylmethacrylate, 3-hydroxy-2-ethylhexylacrylate, 3-hydroxy-2-ethylhexylmethacrylate etc.

Suitable additional monomers c) are also primary amides of alpha, beta-ethylenically unsaturated monocarboxylic acids and N-alkyl and N,N-dialkyl derivatives thereof, such as acrylamide, methacrylamide, N-methyl(meth)acrylamide, N-ethyl(meth)acrylamide, N-propyl(meth)acrylamide, N-(n-butyl)(meth)acrylamide, N-(tert-butyl)(meth)acrylamide, N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth)acrylamide, N-nonadecyl(meth)acrylamide, N-arachinyl(meth)acrylamide, N-behenyl(meth)acrylamide, N-lignoceryl(meth)acrylamide, N-cerotinyl(meth)acrylamide, N-melissinyl(meth)acrylamide, N-palmitoleinyl(meth)acrylamide, N-oleyl(meth)acrylamide, N-linolyl(meth)acrylamide, N-linolenyl(meth)acrylamide, N-stearyl(meth)acrylamide, N-lauryl(meth)acrylamide, N,N-dimethyl(meth)acrylamide, N,N-diethyl(meth)acrylamide, morpholinyl(meth)acrylamide.

Suitable additional monomers c) are also N-vinyllactams and derivatives thereof, which can have e.g. one or more $C_1$-$C_6$-alkylsubstituents, such as methyl, ethyl, n-propyl, isopropyl, n-butyl, sec-butyl, tert-butyl etc. These include e.g. N-vinyl pyrrolidone, N-vinyl piperidone, N-vinyl caprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. Preference is given to using N-vinyl pyrrolidone and N-vinyl caprolactam.

Open-chain N-vinyl amide compounds suitable as monomers c) are, for example, N-vinyl formamide, N-vinyl-N-methylformamide, N-vinylacetamide, N-vinyl-N-methylacetamide, N-vinyl-N-ethylacetamide, N-vinyl propionamide, N-vinyl-N-methylpropionamide and N-vinyl butyramide.

Suitable additional monomers c) are also vinylacetate, vinyl propionate, vinyl butyrate and mixtures thereof.

Suitable additional monomers c) are also ethylene, propylene, isobutylene, butadiene, styrene, alpha-methylstyrene, acrylonitrile, methacrylonitrile, vinylchloride, vinylidene chloride, vinylfluoride, vinylidene fluoride and mixtures thereof.

The additional monomers c) specified above can be used individually or in the form of any desired mixtures.

To produce the aqueous polymer dispersions, the component c) is used preferably in an amount of from 0 to 80% by weight, based on the total weight of the monomers used for the polymerization. A specific embodiment relates to polymer dispersions Pd) which comprise no additional monomer c) in copolymerized form. If present, the component c) is used preferably in an amount of from 0.1 to 70% by weight, particularly preferably 1 to 60% by weight, in particular 5 to 50% by weight, based on the total weight of the monomers used for the polymerization.

Preferably, no monomer c) is used.

Monomer d)

The monomer mixtures M) used to produce the polymer dispersions can comprise, in copolymerized form, in addition to the compound a), at least one further compound d) different there from having a free-radically polymerizable alpha,beta-ethylenically unsaturated double bond and at least one cationogenic and/or cationic group per molecule.

Preferably, the cationogenic or cationic groups of component d) are nitrogen-containing groups, such as primary, secondary and tertiary amino groups and quaternary ammonium groups. Preferably, the nitrogen-containing groups are tertiary amino groups or quaternary ammonium groups. Charged cationic groups can be produced from the amine nitrogens either by protonation, e.g. with monobasic or polybasic carboxylic acids, such as lactic acid or tartaric acid, or mineral acids, such as phosphoric acid, sulfuric acid and hydrochloric acid, or by quaternization, e.g. with alkylating agents, such as $C_1$-$C_4$-alkylhalides or sulfates. Examples of such alkylating agents are ethylchloride, ethylbromide, methylchloride, methylbromide, dimethylsulfate and diethylsulfate.

Suitable compounds d) are e.g. the esters, different from DEAEMA, of alpha, beta-ethylenically unsaturated mono- and dicarboxylic acids with amino alcohols. Preferred amino alcohols are $C_2$-$C_{12}$-aminoalcohols which are $C_1$-$C_8$-mono- or dialkylated on the amine nitrogen. Suitable acid components of these esters are e.g. acrylic acid, methacrylic acid, fumaric acid, maleic acid, itaconic acid, crotonic acid, maleic anhydride, monobutylmaleate and mixtures thereof. Preference is given to using acrylic acid, methacrylic acid and mixtures thereof as acid component of these esters.

Suitable additional compounds d) are N,N-dimethylaminomethyl(meth)acrylate, N,N-dimethylaminoethyl(meth)acrylate, N,N-diethylaminoethylacrylate, N,N-dimethylaminopropyl(meth)acrylate, N,N-diethylaminopropyl(meth)acrylate and N,N-dimethylaminocyclohexyl(meth)acrylate.

Suitable monomers d) are also the amides of the aforementioned alpha, beta-ethylenically unsaturated mono- and dicarboxylic acids with diamines which have at least one primary or secondary amino group. Preference is given to diamines which have one tertiary and one primary or secondary amino group.

These include N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc.

Suitable monomers d) are also N,N-diallylamines and N,N-diallyl-N-alkylamines and acid additions salts and quaternization products thereof. Alkyl here is preferably $C_1$-$C_{24}$-alkyl. Preference is given to N,N-diallyl-N-methylamine and N,N-diallyl-N,N-dimethylammonium compounds, such as e.g. the chlorides and bromides.

Suitable monomers d) are also vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and the salts thereof.

To produce the aqueous polymer dispersions Pd), the monomer d), if present, is used preferably in an amount such that the sum of the amounts of the monomers a) and of the monomers d) is in a range from 25 to 65% by weight, particularly preferably 30 to 60% by weight, based on the total weight of the monomers used for the polymerization.

To produce the aqueous polymer dispersions Pd), the component d) is used preferably in an amount of from 0 to 50% by weight, based on the total weight of the monomers used for the polymerization.

As already explained, it has surprisingly been found that the polymer dispersions Pd) used according to certain embodiments of the invention, based on DEAEMA (component a)), have a particularly good profile of properties. This profile of properties can as a rule be achieved without using further monomers having cationogenic/cationic groups. One specific embodiment therefore relates to polymer dispersions Pd) that do not comprise an additional monomer d) in copolymerized form.

If present, the component d) is used preferably in an amount of from 0.1 to 40% by weight, particularly preferably 1 to 30% by weight, in particular 2 to 25% by weight, based on the total weight of the monomers used for the polymerization.

In one particularly preferred embodiment of the process according to the invention, a monomer mixture M) is used that consists of
   43 to 47% by weight, based on the total weight of the monomers used for the polymerization, of N,N-diethylaminoethylmethacrylate a), and
   53 to 57% by weight, based on the total weight of the monomers used for the polymerization, of at least one compound b), in particular methylmethacrylate.

As regards the preparation of the polymers by free-radical emulsion polymerization, reference is made here expressly to the disclosure of WO 2009/016258, in which the preparation and preferred embodiments are described in detail.

The polymers present in the dispersions preferably have an average molecular weight $M_w$, determined by means of gel permeation chromatography, in the range from 30 000 to 500 000, particularly preferably 60 000 to 140 000, in particular 80 000 to 120 000 g/mol.

The polymers present in the dispersions Pd) preferably have a K value (determined in accordance with Fikentscher on a 1% strength solution in N-methylpyrrolidone (NMP)) in the range from 40 to 60.

The glass transition temperature $T_G$ (determined by means of DSC) is preferably in a range from 40 to 70° C., particularly preferably 52 to 62° C.

The polymers present in the dispersions are essentially random copolymers.

The average particle diameter of the polymer particles present in the polymer dispersion (determined by means of analytical ultracentrifuge) is preferably in a range from 70 to 200 nm, particularly preferably from 80 to 150 nm, in particular from 90 to 120 nm. The particle size distribution is preferably essentially unimodal.

The LT value of the dispersions, determined on a 0.01% strength dispersion in water (2.5 cm cuvette, white light) is preferably at least 70%, particularly preferably at least 80%. Determination of the light transmission is described e.g. in Dieter Distler, Wässrige Polymerdispersionen [Aqueous polymer dispersions], Wiley-VCH (1999), p. 40.

The solids content of the dispersions is preferably 10 to 50% by weight, particularly preferably 20 to 40% by weight. In the case of a purification of the dispersion by means of ultrafiltration, the dispersions preferably have solids contents that are within these ranges before and after the ultrafiltration. It is of course likewise possible to subject a diluted polymer dispersion to a concentration by ultrafiltration.

The dispersions used for taste masking have, e.g. even at a solids content of 30% by weight, extremely low viscosities of preferably less than 50 mPas, particularly preferably less than 25 mPas and in particular less than 10 mPas (values determined by means of Brookfield viscometer at 20° C. and 100 s$^{-1}$). Such low viscosities are of particular importance for many applications.

The charge of the polymers present in the dispersions according to the invention is dependent on the pH of the dispersion. The isoelectric point is preferably in a pH range from about 7.5 to 8.5. The finished dispersion preferably has a pH in the range from 8 to 10, particularly preferably from 8.5 to 9.5 (at a solids content of 30% by weight). It is advantageous for the pH of the finished dispersion to be selected higher (more alkaline) than its isoelectric point provided dissolution or swelling of the polymer particles present in the dispersion is not desired. The dispersions are therefore preferably basic dispersions.

The polymer dispersions are notable for their pH-dependent solubility. The pH range in which the dispersion dissolves upon acidification can be adjusted e.g. by the copolymerized amount of N,N-diethylaminoethylmethacrylate (monomer a) and optionally the use of further monomers with cationogenic/cationic groups (monomer d). Preferably, the polymers present in the polymer dispersions Pd) dissolve at a pH of at most 6.8, particularly preferably at a pH of at most 6.0.

According to one preferred embodiment, polymer dispersions are used which comprise a polymer which comprises, in copolymerized form,
   43 to 47% by weight, based on the total weight of the monomers used for the polymerization, of N,N-diethylaminoethylmethacrylate a), and
   53 to 57% by weight, based on the total weight of the monomers used for the polymerization, of at least one compound b)
as the only monomers.

Component B

The coating compositions of the outer layer comprise, in addition to the polymer, one or more antioxidants or a combination of antioxidants.

Of suitability in principle for improving the release stability as antioxidants are primarily the following agents, listed combinations or further combinations:
N-acetylcysteine, allantoin, arginine, arginine+butylhydroxytoluene, arginine+N-acetylcysteine, ascorbylpalmitate, aspartic acid, biotin, butylhydroxyanisole, butylhydroxytoluene, butylhydroxytoluene+calcium carbonate, butylhydroxytoluene+Na-EDTA, butylhydroxytoluene+N-acetylcysteine calcium-bis[monoethyl(3,5-di-tert-butyl-4-hydroxybenzyl)phosphonate], catechol, citric acid, cysteamine, ethylhexylthioglycolate, gallic acid, hypophosphorous acid, caffeic acid, potassium iodide, creatine, creatinine, copper(I)chloride, copper(II)chloride, lysine, MEHQ, methionine, Na-EDTA, sodium carbonate, sodium dihydrogenphosphate, disodium hydrogenphosphate, sodium propionate, nordihydroguaiaretic acid, orotic acid, penicillamine, phosphoric acid, propylgallate, resveratrol, riboflavin, spermidine, thioglycolic acid, tocopherol, tocopherolacetate, trometamol, tyrosine, tartaric acid.

Of suitability in principle for improving the stability against yellowing are primarily the following agents, listed combinations or further combinations:
oleic acid, simethicone, butylhydroxytoluene, sodiumhydrogensulfite, tocopherol, sodium dihydrogencitrate, sodium hypochlorite, sodium hypophosphite, disodium hydrogenphosphate, tocopherol, tocopherolacetate, arginine, butylhydroxytoluene+Na-EDTA, acetylcysteine (N-acetylcysteine), butylhydroxytoluene, allantoin, butylhydroxyanisole, sodium carbonate, cysteamine, N-acetylcysteine.

Preferred antioxidants are compounds of the phenol type. Preferred phenolic compounds are, for example, butylhydroxytoluene or butylhydroxyanisole, as they completely prevent both delay in dissolution and yellowing. Further suitable products are: catechol, gallic acid or esters thereof, tocopherol, caffeic acid, hydroquinone monomethylether (MEHQ), nordihydroguaiaretic acid, resveratrol.

Likewise preferred antioxidants are thiolic compounds, such as N-acetylcysteine, cysteamine, thioglycolic acid.

Furthermore, preference is given to basic amino acids such as arginine and lysine.

Preferred antioxidants are also alkali metal carbonates or alkali metal bicarbonates, in particular the sodium salts, preferably sodium carbonate.

Preference is also given to combinations with EDTA, in particular Na-EDTA or with citric acid.

Particular preference is given to N-acetylcysteine, arginine, lysine, butylhydroxytoluene, butylhydroxytoluene+Na EDTA, and also sodium carbonate or combinations thereof.

All of the stated compounds or classes of compounds can also be used in combination.

The antioxidants are used in amounts of from 0.1 to 30, preferably 0.3 to 20, particularly preferably 0.5 to 12% by weight, based on the total amount of the solid in the coating composition.

Component C

Furthermore, the coating compositions according to the invention comprise plasticizers, preferably lipophilic plasticizers, as component C. Particularly suitable plasticizers are tributylcitrate, acetyltributylcitrate, acetyltriethylcitrate, triacetin, triethylcitrate, diethylsebacate and dibutyl sebacate.

Components D

The coating compositions used according to the invention for pharmaceutical administration forms can comprise, as components D, additionally at least one further pharmaceutically acceptable excipient. Of pharmaceutical acceptability are the excipients known for use in the field of pharmacy, food technology and related fields, in particular those listed in the relevant pharmacopoeia (e.g. Ph. Eur., USP, JP), and other excipients whose properties do not prohibit a physiological application.

Suitable excipients may be: aroma substances, taste-improving substances, sweetening agents (sugars, sugar alcohols, sweeteners such as e.g. aspartame, saccharine-Na, sodium cyclamate), glidants, wetting agents, release agents, anti-adhesives, stabilizers, pore formers, neutralizing agents, gloss agents, dyes, pigments, disinfectants or preservatives, thickeners, etc. Such substances are described e.g. in Fiedler, H. P. Lexikon der Hilfsstoffe fürPharmazie, Kosmetikund angrenzende Gebiete [Lexicon of excipients for pharmacy, cosmetics and related fields], 4th edition, Aulendorf: ECV-Editio-Cantor-Verlag, 1996.

Customary amounts of the excipients are in a range of in each case from 0 to 70% by weight, preferably from 0 to 60% by weight, in particular 1 to 50% by weight, based on the total weight of the solid in the coating composition.

The coating compositions which are used for producing the outer coating layer can comprise, based on the total weight of the aqueous dispersion,
  i) 1 to 45% by weight of component A,
  ii) 0.01 to 15% by weight of component B,
  iii) 0.1 to 15% by weight of component C,
  iv) 0 to 35% by weight of components D.

Preferred coating compositions comprise
  i) 1.5 to 42.5% by weight of component A,
  ii) 0.02 to 10% by weight of component B,
  iii) 0.15 to 12.5% by weight of component C,
  iv) 0 to 30% by weight of components D.

Particularly preferred coating compositions comprise, based on the total weight of the dispersion,
  i) 4 to 40% by weight of component A,
  ii) 0.05 to 6% by weight of component B,
  iii) 0.4 to 8% by weight of component C,
  iv) 0.1 to 20% by weight of components D.

The coating compositions both for the inner and outer layer can be produced e.g. by intimate mixing of a polymer dispersion or polymer solution, or a polymer obtainable there from by a drying process.

The coating compositions can be used e.g. in powder form, as melt or in aqueous emulsion by granulation, pouring, spreading or by means of spray application. Preference is given to application as polymer dispersion, specifically as primary dispersion. The coating compositions can additionally comprise at least one further polymer component. In this connection, it is possible to use mixtures of at least two dispersions, at least one dispersion and at least one solution, at least one dispersion and at least one powder, at least two powders, etc.

The coating compositions according to the invention are suitable for dosage forms of in principle any desired pharmaceutical active ingredients with acidic groups, which can preferably be administered in isolated or protected form, such as antidepressants, beta receptor blockers, anti-diabetics, analgesics, antiphlogistics, antirheumatics, antihypotonics, antihypertonics, psychopharmaceuticals, tranquilizers, antiemetics, muscle relaxants, glucocorticoids, agents for treating Colitis ulcerosa or Crohn's disease, antiallergics, antibiotics, antiepileptics, anticoagulants, antimycotics, antitussives, arteriosclerosis drugs, diuretics, enzymes, enzyme inhibitors, gout remedies, hormones and inhibitors thereof, cardiac glycosides, immunotherapeutics and cytokines, laxatives, antilipemics, gastrointestinal therapeutics, migraine remedies, preparations of minerals, otologics, Parkinson's drugs, thyroid therapeutics, spasmolytics, platelet aggregation inhibitors, vitamins, cytostatics and metastasis inhibitors, phytopharmaceuticals, chemotherapy drugs, nutraceuticals, vitamins, carotenoids and amino acids.

Examples of suitable acidic active ingredients are: aceclofenac, acediasulfone, acedoben, aceglutamide, acemetacin, acetoxyvalerenic acid, acetylcysteine, acetylleucine, acetylmethionine, acetylsalicylic acid, acexamic acid, acifluorfen, acipimox, acitazanolast, acitretin, aconiazide, acrivastine, actarit, adapalene, adipiodone, alacepril, alatrofloxacin, alclofenac, alitame, alitretinoin, alliin, alminoprofen, alprostadil, alvimopan, amfenac, amineptine, aminocaproic acid, aminohippuric acid, 5-aminolevulinic acid, aminomethylbenzoic acid, aminopyralid, aminosalicylic acid, amlexanox, amoxicillin, ampicillin, amphotericin B, argatroban, arsenamide, artesunate, aspartame, aspoxicillin, atorvastatin, aurintricarboxylic acid, aurothiomalic acid, aviglycine, aviptadil, azelaic acid, azidocillin, azlocillin, azoximer bromide, aztreonam, baclofen, balofloxacin, balsalazide, benazepril, benazolin, bendamustine, bendazac, bensuldazic acid, bensulfuron, bentazon, bentiacide, bentiromide, benzylpenicilline, phenoxymethylpenicilline, bepotastine, beraprost, betamipron, betanin, bexarotene, bezafibrate, bilanafos, biotin, bivalirudin, beta-boswellic acid, bromfenac, bucillamine, bumadizone, bumetanide, buthiopurine, butibufen, C12 peptide, calcitonin, canrenoic acid, capobenic acid, captopril, carbenicillin, carbenoxolone, carbidopa, carbocisteine, carboprost, carfecillin, carfentrazone, carglumic acid, carindacillin, carnosine, carprofen, carumonam, carzenide, cefacetrile, cefaclor, cefadroxil, cefalexin, cefaloglycin, cefaloridine, cefalotin, cefamandole, cefapirin, cefatrizine, cefazolin, cefbuperazone, cefdinir, cefepime, cefixime, cefinenoxime, cefinetazole, cefminox, cefodizime, cefonicid, cefoperazone, ceforanide, cefoselis, cefotaxime, cefotetan, cefotiam, cefovecin, cefoxazole, cefoxitin, cefozopran, cefpimizole, cefpiramide, cefprozil, cefradine, cefroxadine, cefsulodin, ceftazidime, ceftezole, ceftibuten, ceftiofur, ceftizoxime, ceftriaxone, cefuroxime, cefuzonam, ceruletide, cetirizine, cetraxate, chenodeoxycholic acid, chloramben, chlorambucil, chondroitin sulfate, chromocarb, ciclacilin, cicloxilic acid, cilastatin, cilazapril, cinametic acid, cinoxacin, ciprodex, ciprofibrate, ciprofloxacin, clanobutin, clavulanic acid, clidanac, clinofibrate, clofencet, clonixin, cloprop, clopyralid, clorazepate, cloxacillin, cloxyfonac, corticorelin, cromoglicic acid, cyclanilide, cyclobutyrol, cynarine, dalapon, daminozide, danofloxacin, daptomycin, deferasirox, dehydrocholic acid, delapril, dexibuprofen, dexketopropfen, dexlipotam, dextrothyroxine, diacerein, dibromotyrosine, dicamba, dichlorprop, dichlorprop-P, diclofenac, diclofop, dicloxacillin, difenoxin, difloxacin, diflufenzopyr, diflunisal, diiodotyrosine, dikegulac, dimecrotic acid, dinoprost, dinoprostone, divalproex, D-luciferin, doconexent, doripenem, D-penicillamine, D-droxidopa, ecabet, eflornithine, eltenac, eltrombopag, enalapril, enalaprilat, endothal, enfenamic acid, enfuvirtide, enkorten, enoxacin, enoxolone, enrofloxacin, epalrestat, epoetin alfa, epoprostenol, eprosartan, eptifibatide, erdosteine, ertapenem, erythrosine, escin, etacrynic acid, etodolac, exenatide, faropenem, febuxostat, felbinac, fenbufen, fenchlorazole, fencibutirol, fendizoic acid, fenofibric acid, fenoprofen, fenoxaprop, fenoxaprop-P, fentiazac, fexofenadine, flavodic acid, fleroxacin, flomoxef, fluazifop, fluazifop-P, flucloxacillin, flufenamic acid, flumequine, flumiclorac, flunixin, flunoxaprofen, fluorodopa F18, flupropanate, fluprostenol, flupyrsulfuron, flurbiprofen, folic acid, folinic acid, fostosal, fosinopril, fudosteine, fumagillin, furosemide, fusidic acid, gabapentin, gadobenic acid, gadobutrol, gadodiamide, gadofosveset, gadopentetic acid, gadoteric acid, gadoxetic acid, gamma-aminobutyric acid, gamolenic acid, garenoxacin, gatifloxacin, gemfibrozil, gemifloxacin, gentisic acid, gibberrellic acid, gibberellin A4, gibberellin A7, glucagon, glufosinate, glycopine, glycyrrhizin, glyphosate, halazone, hetacillin, hyaluronic acid, ibafloxacin, ibuprofen, icatibant, icosapent, iloprost, imazamox, imazapic, imazapyr, imazaquin, imazethapyr, imidapril, imipenem, indium In-111 pentetreol, indobufen, indol-3-ylacetic acid, indolebutyric acid, indometacin, invicorp, iocetamic acid, iodamidelodoxamic acid, ioglicic acid, iopanoic acid, iotalamic acid, iotroxic acid, ioxaglic acid, ioxitalamic acid, ipodic acid, isotretinoin, karetazan, alpha-ketoglutaric acid, ketoprofen, ketorolac, lactobionic acid, lasalocid A, latamoxef, letosteine, levo carnitine acetate, levocabastine, levocetirizine, levofloxacin, levofolinic acid, levomefolic acid, levopropicillin, levothyroxine, limaprost, liothyronine, liraglutide, lisinopril, lobenzarit, lodoxamide, lomefloxacin, lonazolac, lonidamine, loracarbef, loxoprofen, lubiprostone, lumiracoxib, luprostiol, lusupultide, lymecycline, marbofloxacin, mecillinam, meclofenamic acid, mecoprop-P, mefenamic acid, mefenpyr-diethyl, mefolinate, meglutol, meloxicam, melphalan, mepifylline, meropenem, mesalazine, metadoxine, metampicillin, methotrexate, methyldopa, metiazinic acid, meticillin, metirosine, metsulfuron, mezlocillin, midoriamin, miloxacin, mitiglinide, moexipril, mofezolac, monensin, montelukast, moxifloxacin, mupirocin, mycophenolic acid, nadifloxacin, nadroparin, nafcillin, nalidixic acid, naphthalene-1-acetic acid, naproxen, naptalam, narasin, natamycin, nateglinide, nedocromil, nesiritide, nicotinic acid, niflumic acid, nisin, norfloxacin, N-phenylphthalamic acid, nystatin, ofloxacin, olopatadine, olsalazine, orazamide, orbifloxacin, orotic acid, oxaceprol, oxacillin, oxaprozin, oxitriptan, oxolinic acid, ozagrel, pamoic acid, panipenem, pantothenic acid, parahydroxycinnamic acid, pasiniazid, pazufloxacin, pefloxacin, peforelin, pelargonic acid, pemetrexed, penicillin G, peramivir, perindopril, phenethicillin, phenoxymethylpenicillin, photofrin, phthalylsulfathiazole, picloram, pidolic acid, pidotimod, pipemidic acid, piperacillin, pirenoxine, piretanide, piromidic acid, piroxicam, pirprofen, pivagabine, pralatrexate, pranoprofen, pregabalin, primisulfuron-methyl, probenecid, procodazole, proglumide, prohexadione, propagermanium, propicillin, protizinic acid, prulifloxacin, pyrazosulfuron, pyrithiobac, quinapril, quinaprilat, quinclorac, quinmerac, quizalofop, quizalofop-P, raltitrexed, ramatroban, ramipril, ranelic acid, rebamipide, repaglinide, rhodamine B, ritiometan, robenacoxib, romurtide, rosoxacin, rotraxate, (R)-trolox, rufloxacin, salicylic acid, salinomycin, salsalate, sarafloxacin, sarpogrelate, semax, semduramicin, seratrodast, sincalide, sivelestat, sofalcone, somatorelin, somatostatin, sorbic acid, spaglumic acid, sparfloxacin, spirapril, stepronin, stibogluconic acid, (S)-trolox, sugammadex, sulbactam, sulbenicillin, sulfasalazine, sulfasuccinamide, sulfometuron, sulfosate, sulindac, suprofen, suxibuzone, talaporfin, tamibarotene, tazobactam, teclofta-lam, teicoplanin, telmesteine, telmisartan, temocapril, temocillin, tenoic acid, teriparatide, tetracosactide, thioctic acid, thiomersal, thymalfasin, tiagabine, tianeptine, tiaprofenic acid, tiaprost, ticarcillin, tidiacic, timonacic, tiopronin, tiratricol, tirofiban, tocamphyl, tolfenamic acid, tolmetin, tolylphthalamic acid, tosufloxacin, trafermin, trandolapril, tranexamic acid, tranilast, trepibutone, treprostinil, tretinoin, tribenuron, triclopyr, tridecactide, triflusal, triflusulfuron, trolox, tropesin, trovafloxacin, ubenimex, undecylenic acid, ursodeoxycholic acid, valerenic acid, valproic acid, valsartan, vancomycin, vebufloxacin, vedaprofen, verteporfin, vigabatrin, zaltoprofen, zanamivir, ziconotide, zofenopril.

Many of these active ingredients have a bitter or unpleasant taste.

If desired, the active ingredients can also be used in the form of their pharmaceutically acceptable modifications or derivatives, and in the case of chiral active ingredients it is possible to use either optically active isomers or racemates or diastereoisomer mixtures. If desired, the compositions according to the invention can also comprise two or more pharmaceutical active ingredients.

According to the invention, the coating compositions for the coating of cores comprising acidic active ingredients can be used in the form of extrudates, minitablets, granules, pellets, micropellets or crystals. The cores can also consist of nonpareils which have been coated with the acidic active ingredient.

To produce dosage forms, the coated active-ingredient-containing cores can be mixed with suitable auxiliaries and compacted to give tablets which disintegrate in the aqueous environment of the oral cavity and release the coated fine shaped articles. Of particular importance here are the so-called oral dispersibles, i.e. tablets which disintegrate in the mouth within a short time and release the small shaped articles provided with the coatings according to the invention.

Furthermore, the coating compositions can also advantageously be used for coating tablets.

The excellent taste masking results from the insolubility of the polymers according to the invention at pHs above 6 and the rapid solubility at pHs below 6. I.e., in the saliva (pH: 7.2) correspondingly coated forms are stable for a very long time and there is no contact of the bitter pharmaceutical with the oral mucosa, but in the stomach at pHs of 1 to 5, a very rapid release of the active ingredient takes place. Dissolution is then so rapid that there is no difference in the onset of action compared with an uncoated form. As a rule, film coatings of a polymer according to the invention dissolve within min in gastric juice, whereas in phosphate buffer pH 7.2 they are stable over 2 hours. Surprisingly, the film coatings also dissolve relatively quickly in media with pHs of 4.5, meaning that the dosage forms produced therefrom develop a rapid action even in the case of an acidic patients or patients being treated with antacids.

The coating compositions according to the invention have good stability against variation in release under thermal stress. In many cases, the stability against yellowing is also marked. Furthermore, the water vapor permeability is also advantageously influenced.

EXAMPLES

Abbreviations Used
BHT: butylhydroxybenzene
NAC: N-acetylcysteine
ATBC: acetyltributylcitrate
TEC: triethylcitrate
MEHQ: hydroquinone monomethylether
d: days
demin.: demineralized
Ludipress®: formulated product of lactose (90%), povidone (3.5%) and crospovidone (3.5%)
Avicel® PH 102: microcrystalline cellulose
Kollidon® VA 64: vinylpyrrolidone—vinylacetate (6:4) copolymer (copovidone)
Kollidon® CL: crosslinked polyvinylpyrrolidone (crospovidone)
Kollicoat® IR: polyvinylalcohol—polyethylene glycol 6000 graft polymer (weight ratio PVA:PEG 75:25, degree of saponification 94 mol %), molecular weight: 45 000 Daltons All data in % relate to % by weight, unless stated otherwise.
Cationic Polymers:
The preparation of the polymers takes place analogously to Example 1 in WO 2009/016258.
Polymer A: methylmethacrylate/diethylaminoethylmethacrylate, weight ratio 60:40,
Polymer B: methylmethacrylate/diethylaminoethylmethacrylate, weight ratio 55:45
Polymer C: methylmethacrylate/diethylaminoethylmethacrylate, weight ratio 53:47
The K values measured at 0.1 strength by weight in NMP were 50+/−0.5

The polymers were used as 30% strength by weight aqueous dispersions with a pH of 9+/−0.3. The average particle size of the primary dispersion was 110 nm.

The determination of the release from administration forms was carried out using the instrument with paddle stirrer described in the Pharmacopoeia of the USA (USP 32) under Dissolution.

Example 1

Coated Acetylsalicylic Acid Tablet 100 mg
Formulation of the Tablet:

| | |
|---|---|
| Ludipress | 189 mg |
| Avicel PH 101 | 40 mg |
| Acetylsalicylic acid | 100 mg |
| Stearic acid | 1 mg |
| Tablet weight | 330 mg |
| Method | direct tabletting |
| Tablet shape | convex |
| Diameter | 9 mm |

Spray Formulation for Inner Layer:

| | |
|---|---|
| Kollicoat IR | 12% |
| Talc | 8% |
| Demin. Water | 80% |
| Solids content | 20% |

Coating Conditions:

| | |
|---|---|
| Machine | Accela Cota 24/ horizontal drum coater |
| Inlet air temperature | 55° C. |
| Spraying pressure | 2.5 bar |
| Shaping air pressure | 1 bar |
| Spray die | Schlick 930/1 mm |
| Air supply rate | 200 m$^3$/h |
| Charge | 7 kg |
| Spraying rate | 30 g/min |
| Application rate | 1.5 mg/cm$^2$ |

Spray Formulation for Outer Layer:

| | |
|---|---|
| Polymer B (30% strength dispersion) | 33.33% |
| Tributylcitrate | 1.50% |
| Butylhydroxytoluene | 0.5 |
| Talc | 6% |
| Titanium dioxide | 2% |
| Demin. water | 56.67% |
| Solids content | 20% |

Coating Conditions:

| | |
|---|---|
| Machine | Accela Cota 24/ horizontal drum coater |
| Inlet air temperature | 55° C. |
| Spraying pressure | 2 bar |
| Shaping air pressure | 1 bar |
| Spray die | Schlick 930/1 mm |
| Air supply rate | 200 m$^3$/h |
| Charge | 7 kg |
| Spraying rate | 30 g/min |
| Application rate | 4.5 mg/cm$^2$ |

Result:

Release in Acetate Buffer pH 4.5

| Time in min | Starting value in % | 3 months 30/70% r.h. in % | 3 months 40° C. in % |
| --- | --- | --- | --- |
| 15 | 73.5 | 74.6 | 73.9 |
| 30 | 99.8 | 98.9 | 99.5 |
| 60 | 100.2 | 100.3 | 99.7 |

Release in Phosphate Buffer pH 6.8

| Time in min | Starting value in % | 3 months 30/70% r.h. in % | 3 months 40° C. in % |
| --- | --- | --- | --- |
| 15 | 0.2 | 0.3 | 0.4 |
| 30 | 0.3 | 0.3 | 0.3 |
| 60 | 0.4 | 0.5 | 0.6 |

Further Properties

| | Starting value | 3 months 30/70% r.h. | 3 months 40° C. |
| --- | --- | --- | --- |
| Appearance | Smooth, shiny, no adhesion, no damage | Smooth, shiny, no adhesion, no damage | Smooth, shiny, no adhesion, no damage |
| Taste test | No bitter taste after 5 min in the mouth | No bitter taste after 5 min in the mouth | No bitter taste after 5 min in the mouth |

Comparative Example to 1

Preparation Analogous to Example 1 but without the Inner Layer

Release in Acetate Buffer pH 4.5

| Time in min | Starting value in % | 3 months 30/70% r.h. in % | 3 Months 40° C. in % |
| --- | --- | --- | --- |
| 15 | 72.5 | 81.5 | 89.7 |
| 30 | 99.6 | 98.5 | 99.1 |
| 60 | 99.8 | 100.3 | 99.9 |

Release in Phosphate Buffer pH 6.8

| Time in min | Starting value in % | 3 months 30/70% r.h. in % | 3 months 40° C. in % |
| --- | --- | --- | --- |
| 15 | 0.4 | 12.3 | 10.6 |
| 30 | 1.8 | 25.7 | 23.4 |
| 60 | 3.9 | 54.8 | 49.8 |

Further Properties

| | Starting value | 3 months 30/70% r.h. | 3 months 40° C. |
| --- | --- | --- | --- |
| Appearance | Smooth, shiny, no adhesion, no damage | Rough, matt, tablets stick, significant damage | Rough, matt, tablets stick, significant damage |
| Taste test | No bitter taste after 5 min in the mouth | Bitter taste after 0.5 min in the mouth | Bitter taste after 0.5 min in the mouth |

Example 2

Coated Ibuprofen Tablet 200 mg

Formulation of the Tablet:

| | |
| --- | --- |
| Ibuprofen | 200 mg |
| Avicel PH 101 | 142.5 mg |
| Kollidon CL | 10 |
| Aerosil 200 | 6 |
| Magnesium stearate | 1.5 mg |
| Tablet weight | 360 mg |
| Method | Direct tabletting |
| Tablet shape | convex |
| Diameter | 9 mm |

Spray Formulation for Inner Layer:

| | |
| --- | --- |
| Kollicoat IR | 12% |
| Talc | 8% |
| Demin. water | 80% |
| Solids content | 20% |

Coating Conditions:

| | |
| --- | --- |
| Machine | Accela Cota 24/ horizontal drum coater |
| Inlet air temperature | 55° C. |
| Spraying pressure | 2.5 bar |
| Shaping air pressure | 1 bar |
| Spray die | Schlick 930/1 mm |
| Air supply rate | 200 m³/h |
| Charge | 7 kg |
| Spraying rate | 30 g/min |
| Application rate | 1.5 mg/cm² |

Spray Formulation for Outer Layer:

| | |
| --- | --- |
| Polymer A (30% strength dispersion) | 33.33% |
| Acetyltriethyl citrate | 1.50% |
| Butylhydroxytoluene | 0.5 |
| Talc | 6% |
| Titanium dioxide | 2% |
| Demin. water | 56.67% |
| Solids content | 20% |

Coating Conditions:

| | |
| --- | --- |
| Machine | Accela Cota 24/ horizontal drum coater |
| Inlet air temperature | 55° C. |
| Spraying pressure | 2 bar |
| Shaping air pressure | 1 bar |
| Spray die | Schlick 930/1 mm |

-continued

| | |
|---|---|
| Air supply rate | 200 m³/h |
| Charge | 7 kg |
| Spraying rate | 30 g/min |
| Application rate | 4.5 mg/cm² |

Result:

Release in Acetate Buffer pH 4.5

| Time in min | Starting value in % | 3 months 30/70% r.h. in % | 3 months 40° C. in % |
|---|---|---|---|
| 15 | 43.4 | 44.6 | 42.9 |
| 30 | 81.8 | 82.6 | 80.5 |
| 60 | 98.9 | 99.9 | 99.2 |

Release in Phosphate Buffer pH 6.8

| Time in min | Starting value in % | 3 months 30/70% r.h. in % | 3 months 40° C. in % |
|---|---|---|---|
| 15 | 0.1 | 0.2 | 0.4 |
| 30 | 0.3 | 0.5 | 0.5 |
| 60 | 0.5 | 0.7 | 0.5 |

Further Properties

| | Starting value | 3 months 30/70% r.h. | 3 months 40° C. |
|---|---|---|---|
| Appearance | Smooth, shiny, no adhesion, no damage | Smooth, shiny, no adhesion, no damage | Smooth, shiny, no adhesion, no damage |
| Taste test | No bitter taste after 5 min in the mouth | No bitter taste after 5 min in the mouth | No bitter taste after 5 min in the mouth |

Example 3

Coated Ibuprofen Minipellets

Composition of the Pellets

| Substance | Composition per pellet [%] |
|---|---|
| Ibuprofen | 100 |

Pellet size 200 to 400 µm

Composition of the Spray Formulation

Spray Formulation for Inner Layer:

| | |
|---|---|
| Kollicoat IR | 12% |
| Talc | 8% |
| Demin. water | 80% |
| Solids content | 20% |

Coating Parameters

Coating was carried out in a fluidized-bed granulator "Glatt GPCG 3.1" from Glatt.

| | |
|---|---|
| Spray nozzle | 1 mm diameter |
| Number of spray nozzles | 1 |
| Filling | 2.5 kg of ibuprofen pellets 200-400 µm |
| Method | Bottom-Spray (Wurster) |
| Spraying pressure | 2.0 bar |
| Inlet air temperature | 55° C. |
| Outlet air temperature | 39° C. |
| Spraying rate | 15 g/min |
| Drying | ca. 5 min |
| Application rate/weight increase | 5% |

Spray Formulation for Outer Layer:

| | |
|---|---|
| Polymer B (30% dispersion) | 33.33% |
| Triethylcitrate | 1.50% |
| Yellow iron oxide | 0.5 |
| Talc | 6% |
| Titanium dioxide | 2% |
| Demin. Water | 56.67% |
| Solids content | 20% |

Coating Parameters

Coating was carried out in a fluidized-bed granulator "Glatt GPCG 3.1" from Glatt.

| | |
|---|---|
| Spray nozzle | 1 mm diameter |
| Number of spray nozzles | 1 |
| Filling | 2.5 kg of ibuprofen pellets 200-400 µm |
| Method | Bottom-Spray (Wurster) |
| Spraying pressure | 1.0 bar |
| Inlet air temperature | 45° C. |
| Outlet air temperature | 29° C. |
| Spraying rate | 15 g/min |
| Drying | ca. 5 min |
| Application rate/weight increase | 20% |

After the coating, the pellets were mixed with 0.2% Aerosil 200 for 10 min in a Turbula mixer.

Result:

Release in Acetate Buffer pH 4.5

| Time in min | Starting value in % | 3 months 30/70% r.h. in % | 3 months 40° C. in % |
|---|---|---|---|
| 15 | 58.2 | 60.0 | 58.1 |
| 30 | 89.5 | 91.2 | 90.5 |
| 60 | 99.7 | 99.9 | 99.2 |

Release in Phosphate Buffer pH 6.8

| Time in min | Starting value in % | 3 months 30/70% r.h. in % | 3 months 40° C. in % |
|---|---|---|---|
| 15 | 0.8 | 0.9 | 1.1 |
| 30 | 1.5 | 1.9 | 1.6 |
| 60 | 2.6 | 2.8 | 2.9 |

Further Properties

|  | Starting value | 3 months 30/70% r.h. | 3 months 40° C. |
|---|---|---|---|
| Appearance | Smooth, no adhesion, no damage | Smooth, no adhesion, no damage | Smooth, no adhesion, no damage |
| Taste test | No bitter taste after 5 min in the mouth | No bitter taste after 5 min in the mouth | No bitter taste after 5 min in the mouth |

Example 4

Coated Ketoprofen Pellets
Formulation of the Pellets:

| Ketoprofen | 20% |
|---|---|
| Avicel PH 101 | 40% |
| Granulac 230 | 40% |
| Method | Extrusion, spheronization |
| Pellet diameter | 0.7-1.4 mm |

Composition of the Spray Formulation
Spray Formulation Inner Layer:

| Kollicoat Protect | 12% |
|---|---|
| Talc | 8% |
| Demin. Water | 80% |
| Solids content | 20% |

Coating Conditions for the Inner Layer:

| Machine | Aeromatic Strea/ Wurster insert |
|---|---|
| Inlet air temperature | 60° C. |
| Spraying pressure | 2.0 bar |
| Nozzle diameter | 0.8 mm |
| Air supply rate | 85-100 m³ |
| Charge | 0.5 kg |
| Spraying rate | 8 g/min |
| Application rate | 1.0 mg/cm² |

Spray Formulation for Outer Layer:

| Polymer C (30% strength dispersion) | 33.33% |
|---|---|
| Tributylcitrate | 1.50% |
| Sunset Yellow AI lake | 0.5 |
| Talc | 6% |
| Titanium dioxide | 2% |
| Demin. water | 56.67% |
| Solids content | 20% |

Coating Conditions for the Outer Layer:

| Machine | Aeromatic Strea/ Wurster insert |
|---|---|
| Inlet air temperature | 52° C. |
| Spraying pressure | 1.3 bar |
| Nozzle diameter | 0.8 mm |
| Air supply rate | 85-100 m³ |
| Charge | 0.5 kg |
| Spraying rate | 8 g/min |
| Application rate | 4.5 mg/cm² |

After the coating, the pellets were mixed with 0.2% Aerosil 200 for 10 min in a Turbula mixer.
Result:
Release in Acetate Buffer pH 4.5

| Time in min | Starting value in % | 3 months 30/70% r.h. in % | 3 months 40° C. in % |
|---|---|---|---|
| 15 | 41.2 | 39.9 | 40.5 |
| 30 | 75.4 | 74.5 | 76.6 |
| 60 | 98.6 | 97.7 | 99.5 |

Release in Phosphate Buffer pH 6.8

| Time in min | Starting value in % | 3 months 30/70% r.h. in % | 3 months 40° C. in % |
|---|---|---|---|
| 15 | 0.8 | 0.9 | 0.6 |
| 30 | 1.3 | 1.2 | 1.1 |
| 60 | 1.8 | 2.0 | 1.5 |

Further Properties

|  | Starting value | 3 months 30/70% r.h. | 3 months 40° C. |
|---|---|---|---|
| Appearance | Smooth, no adhesion, no damage | Smooth, no adhesion, no damage | Smooth, no adhesion, no damage |
| Taste test | No bitter taste after 5 min in the mouth | No bitter taste after 5 min in the mouth | No bitter taste after 5 min in the mouth |

The invention claimed is:
1. A dosage form provided with protective coatings, in which a core comprising at least one acidic active ingredient is provided with at least one inner and one outer coating layer, where the outer layer comprises, as component A, a cationic polymer which is an emulsion polymer of N,N-diethylaminoethyl methacrylate and further monomers,
wherein the inner coating layer comprises a neutral water-soluble polymer comprising polyvinyl alcohols, polyalkylene glycol—polyvinyl alcohol graft copolymers, polyvinylpyrrolidones, vinylpyrrolidone—vinyl acetate copolymers, alkylated and hydroxyalkylated celluloses or starches or mixtures of such polymers, and
wherein component A of the outer coating layer comprises a polymer obtained by free-radical polymerization of:
a) N,N-diethylaminoethyl methacrylate, and
b) at least one free-radically polymerizable compound selected from esters of $\alpha,\beta$-ethylenically unsaturated mono- and dicarboxylic acids with $C_1$-$C_8$-alkanols; and
wherein component A of the outer coating layer comprises a polymer of 43 to 47% by weight, based on the total weight of the monomers used for the polymerization, of N,N-diethylaminoethyl methacrylate a), and 53 to 57% by weight, based on the total weight of the monomers used for the polymerization, of at least one compound b).
2. The dosage form according to claim 1, wherein the at least one acidic active ingredient comprises an active ingredient with free carboxyl, sulfonic acid or phosphonic acid groups, acidic hydroxyl groups, acidic N—H groups or acidic C—H groups or mixtures of these active ingredients.

3. The dosage form according to claim 1, comprising acidic active ingredients with a pKa value between 6.5 and 0.5.

4. The dosage form according to claim 1, comprising acidic active ingredients with a pKa value between 5.0 and 1.0.

5. The dosage form according to claim 1, wherein the neutral polymer of the inner coating layer comprises polyvinyl alcohols, polyalkylene glycol—polyvinyl alcohol graft copolymers or mixtures thereof.

6. The dosage form according to claim 1, wherein component A comprises a polymer obtained with methyl methacrylate as monomer b).

7. The dosage form according to claim 1, wherein the outer coating layer further comprises, as component B, one or more antioxidants.

8. The dosage form according to claim 1, wherein the outer coating layer further comprises, as component B, one or more antioxidants selected from the group consisting of phenolic antioxidants, thiolic antioxidants, basic amino acids, alkali metal carbonates and alkali metal bicarbonates.

9. The dosage form according to claim 1, wherein the outer coating layer further comprises, as component C, one or more plasticizers.

10. The dosage form according to claim 1, wherein the outer coating layer further comprises, as component C, one or more plasticizers selected from the group consisting of tributyl citrate, acetyltributyl citrate, acetyltriethyl citrate, triacetin, triethyl citrate, diethyl sebacate and dibutyl sebacate.

11. The dosage form according to claim 1, wherein the outer coating layer further comprises, as component D, one or more pharmaceutical excipients selected from the group consisting of aroma substances, taste-improving substances, sweeteners, glidants, wetting agents, release agents, antiadhesives, stabilizers, pore formers, neutralizing agents, polishes, dyes, pigments, disinfectants or preservatives, and thickeners.

12. The dosage form according to claim 1, wherein the inner coating layer has a layer thickness of from 1 to 50 μm.

13. The dosage form according to claim 1, wherein the inner coating layer has a layer thickness of from 2 to 25 μm.

14. The dosage form according to claim 1, wherein the inner coating layer has a layer thickness of from 5 to 15 μm.

15. The dosage form according to claim 1, wherein the outer coating layer has a layer thickness of from 5 to 200 μm.

16. The dosage form according to claim 1, wherein the outer coating layer has a layer thickness of from 10 to 150 μm.

17. The dosage form according to claim 1, wherein the outer coating layer has a layer thickness of from 20 to 100 μm.

* * * * *